United States Patent [19]

Nesburn et al.

[11] Patent Number: 5,632,992
[45] Date of Patent: May 27, 1997

[54] PROCESS FOR THE EXPRESSION OF HERPES SIMPLEX VIRUS TYPE 1 GLYCOPROTEIN E AND METHOD OF USE

[75] Inventors: Anthony B. Nesburn, Malibu; Steven L. Wechsler, Westlake Village; Homayon Ghiasi, Los Angeles, all of Calif.

[73] Assignee: Cedars-Sinai Medical Center, Los Angeles, Calif.

[21] Appl. No.: 353,948

[22] Filed: Dec. 9, 1994

Related U.S. Application Data

[63] Continuation of Ser. No. 845,920, Mar. 4, 1992, abandoned, which is a continuation-in-part of Ser. No. 829,947, Feb. 3, 1992.

[51] Int. Cl.$^6$ .................... A61K 39/245; C12N 15/00
[52] U.S. Cl. .................... 424/186.1; 424/231.1; 424/185.1; 435/172.3; 435/235.1
[58] Field of Search .................... 435/235, 172.3, 435/240.2, 69.1; 530/350; 514/2, 12; 424/185.1, 231.1, 186.1

[56] References Cited

U.S. PATENT DOCUMENTS

| | | | |
|---|---|---|---|
| 4,859,587 | 8/1989 | Roizman | 435/69.3 |
| 4,891,315 | 1/1990 | Watson et al. | 435/69.3 |

FOREIGN PATENT DOCUMENTS

| | | |
|---|---|---|
| 0243155 | 10/1987 | European Pat. Off. |
| 0297924 | 1/1989 | European Pat. Off. |
| WO85/04587 | 10/1985 | WIPO |

OTHER PUBLICATIONS

Atherton, "Protection from retinal necrosis by passive transfer of monoclonal antibody specific for herpes simplex virus glycoprotein D," Current Eye Research 11(1):45–52 (1992).

Foster et al., "Immunomodulation of experimental murine herpes simplex keratitis: II. Glycoprotein D protection," Current Eye Research 7(11):1051–1061 (1988).

Ghiasi et al., "Expression of herpes simplex virus type 1 glycoprotein B in insect cells," Virus Research 22(1):35–39 (1991).

Ghiasi et al., "High Level Expression of Each of the Seven Herpes Simplex Virus Glycoproteins in Insect Cells Using Baculovirus Expression Vectors: Subsequent Use as Vaccines," Invest. Ophthalmol. Visual Sci., 32(4):806 (1991).

Ghiasi et al., "Immunoselection of recombinant baculoviruses expressing high levels of biologically active herpes simplex virus type 1 glycoprotein D," Arch. Virol. 121:163–178 (1991).

Kino et al., "Immunogenicity of herpes simplex virus glycoprotein gB–1–related protein produced in yeast,3" Vaccine 7(2):155–160 (1989).

Lausch et al., "Prevention of Herpes Keratitis by Monoclonal Antibodies Specific for Discontinuous and Continuous Epitopes on Glycoprotein D," Ophthal. Visual Sci 32(10):2735–2740 (1991).

Nesburn et al., "Efficacy and Safety of 'Therapeutic' Systemic HSV Vaccines in the Rabbit Ocular Recurrence Model," Invest. Ophthalmol. Visual Sci. 32(4):854 (1991).

Klein, R.J., Reinfections and site–specific immunity in herpes simplex virus infections. Vaccine, 7:380–381 (1989).

Stanberry, L.R. et al., Herpes simplex virus glycoprotein treatment of recurrent genital herpes. J. Infec. Dis., 157:156–63 (1988).

Kern, A.B. et al., Vaccine Therapy in Recurrent Herpes Simplex. Arch. Derm., 89:844–845 (1964).

Frenkel, L. et al., A randomized double blind, placebo–controlled phase 1 trial of a herpes simplex virus purified glycoprotein (gD1) vaccine. Interscience Conf. on Antimicrobial Agents & Chemo., 206 (1990).

Berman, P.W. et al., Efficacy of Recombinant Glycoprotein D Subunit Vaccines on the Development of Primary, Recurrent, and Latent Genital Infections With Herpes Simplex Virus Type 2 in Guinea Pigs. J. Infect. Dis., 157(5):897–902 (May 1988).

Blacklaws, B. et al., Immunogenicity of herpes simplex type 1 glycoproteins expressed in vaccinia virus recombinants. Virology, 177:727–736 (1990).

Stanberry, L.R. et al., Heterologous Versus Homologous Herpes Simplex Virus Glycoprotein Immunotherapy of Recurrent Genital Herpes. Pediatr. Res., 25:191A, Part 2 (1989).

Rock, D.L., Nesburn, A.B. et al., Detection of latency related viral RNAs in trigeminal ganglia of rabbits latently infected with herpes simplex virus type 1. J. Virol., 61:3820–26 (1987).

Matsuura, Y. et al., Baculovirus expression vectors: the requirements for high level expression of proteins, including glycoproteins. J. Gen. Virol., 68:1233–50 (1987).

Lee, G.T. et al., Location of the structural genes for glycoproteins gD and gE and for other polypeptides in the S component of herpes simplex virus type 1 DNA. J. Virol., 43:41–49 (1982).

Mathews, J.T. et al., Synthesis and processing glycoprotein D of herpes simplex virus types 1 and 2 in an in vitro system. J. Virol., 48:521–53 (1983).

Ghiasi, H., et al., Cell surface expression of herpes simplex virus type 1 glycoprotein H in recombinant baculovirus infected cells. Virology, 185:187–194 (1991).

Morein, B. et al., Iscom, a novel structure for antigenic presentation of membrane proteins from enveloped viruses. Nature, 308:457–60 (1984).

(List continued on next page.)

Primary Examiner—Robert A. Wax
Assistant Examiner—Gabriele E. Bugaisky
Attorney, Agent, or Firm—Lyon & Lyon

[57] ABSTRACT

A process for obtaining Herpes Simplex virus type 1 (HSV-1) glycoprotein E (gE) from cells which have been infected or transformed with a recombinant Baculovirus is disclosed. The gE produced is then isolated and purified for use in immunotherapy against HSV infections.

21 Claims, 5 Drawing Sheets

OTHER PUBLICATIONS

Shimormura, Y. et al., Shedding by iontophoresis of 6-hydroxdopamine followed by topical epinephrine. *Invest. Ophthalmol.*, 24:1588–90 (1983).

Nesburn, A.B. et al., Isolation of herpes simplex virus: Isolation from rabbit trigeminal ganglia between episodes of recurrent ocular infection. *Arch. Ophthalmol.*, 88:412–17 (1972).

Nesburn, A.B. et al., Ocular safety and efficacy of an HSV–1 gD vaccine during primary and latent infection. *Invest. Ophthalmol. Vis. Sci.*, 31:77–82 (1990).

Baucke, R.B. and Spear, P.G., Membrane proteins specified by herpes simplex viruses. V. Identification of an Fc–Binding glycoprotein. *J. Virol.* 32:779–789 (1979).

Chatterjee, S., Koga, J. and Whitley, R.J. A role for herpes simplex virus type 1 glycoprotein E in induction of cell fusion. *J. Gen. Virol.*, 70:2157–2162 (1989).

Dubin, G., Frank, I., and Friedman, H.M., Herpes simplex virus type 1 encodes two Fc receptors which have different binding characteristics for monomeric immunoglobulin G (IgG) and IgG complexes. *J. Virol.*, 64:2725–2731 (1990).

Johnson, D.C., Frame, M.C., Ligas, M.W., Cross, A.M. and Stow, N.D., Herpes simplex immunoglobulin G Fc receptor activity depends on a complex of two viral glycoproteins, gE and gI. *J. Virol.*, 62:1347–1354 (1988).

Para, M.F., Baucke, R.B. and Spear, P.G. Glycoprotein gE of Herpes Simplex Virus Type 1: Effects of anti–gE on virion infectivity and on virus induced fC–binding receptors. *J. Virol.*, 41:129–136 (1982).

Goldin et al (1981) J. Virol. 38:50–58.

Eisenberg et al. (1985) J. Virology 56: 1014–1017.

Krishna et al. (1989) J. gen Virol. 70: 1805–1814.

PROCESS FOR THE EXPRESSION OF HERPES SIMPLEX VIRUS TYPE 1 GLYCOPROTEIN E AND METHOD OF USE

This application is a continuation of application U.S. Ser. No. 07/845,920 filed Mar. 4, 1992, now abandoned which is a continuation-in-part of co-pending application Ser. No. 07/829,947, filed Feb. 3, 1992. All of the above applications are expressly incorporated herein by reference.

FIELD OF THE INVENTION

The present invention is in the fields of infectious diseases and molecular biology.

BACKGROUND OF THE INVENTION

A. Herpes Simplex Virus Type 1 (HSV-1) Glycoprotein E

Glycoprotein E (gE) is one of ten documented herpes simplex virus type I (HSV-1) glycoproteins. In HSV-1 infected cells, gE is synthesized as an unglycosylated peptide having a molecular weight of 59 kDa. The unglycosylated polypeptide is cleaved and partially glycosylated to produce a precursor gE (pgE) of approximately 65 kDa, which is then further glycosylated to the mature form of gE with a molecular weight of about 80 kDa.

The ten HSV glycoproteins are located on the surface of the virus, some of which are reported to be the primary inducers and targets of both humoral (antibody) and cell-mediated immune responses to HSV-1 infection. In one study, Blacklaws et al. have shown glycoproteins B and D to induce high neutralizing antibody titers and to protect from latent herpes infection (1). They also found, however, that vaccinia expressed glycoproteins G, H and I produced no protective response in immunized mice (1), and that vaccinia expressed gE demonstrated only a very weak neutralizing antibody response against HSV. Blacklaws et al. also found that vaccination with gE expressed by vaccinia virus did not protect against the establishment of latent infections, nor did it protect mice against lethal HSV-1 challenge (1). In another study, Para et al. found that, only in the presence of complement, antibodies against immunoaffinity purified gE neutralized HSV-1 infectivity. But even then, the neutralization titers were low, and the extent of the anti-gE antibodies' role in neutralization was not determined (2).

In contrast to these reports, we have expressed in a baculovirus system, gE that is capable of eliciting a strong protective immune response against HSV-1 infection. In fact, vaccination with our recombinant baculovirus expressed gE induced high neutralizing antibody titers, a DTH response and protected against lethal HSV-1 challenge in mice. The neutralizing antibody titers we obtained were much higher than titers obtained by either Para et al. against their immunoaffinity purified gE, (2) or Blacklaws et al. against their vaccinia expressed gE (1). In addition, our neutralizing antibody titers against baculovirus expressed gE were only partially complement dependent, which in contrast to Para's results (2), required the presence of complement with their immunoaffinity purified gE for even low neutralizing activity. This ability to produce large quantities of high quality bioactive gE, is critical in the development of an effective vaccine against HSV.

B. DNA Technology

Recombinant DNA and associated technologies can be applied to effectively provide the large quantities of high quality bioactive HSV glycoprotein E required for a therapeutic or prophylactic HSV vaccine.

DNA technology involves in part, producing a replicable expression vehicle or transplacement vector by the DNA recombination of an origin of replication, one or more phenotypic selection characteristics, an expression promoter, a heterologous gene insert and remainder vector. The resulting expression vehicle is introduced into cells by transformation and large quantities of the recombinant vehicle obtained by growing the transformant. Where the gene is properly inserted with reference to portions which govern the transcription and translation of the encoded DNA message, the expression vehicle may produce the polypeptide sequence for which the inserted gene codes. This process of producing the polypeptide is called "expression." The resulting product may be obtained by lysing the host cell, and recovering the product by appropriate purification.

A wide range of host cells can be used, including prokaryotic and eukaryotic organisms. In addition to microorganisms, cultures of cells derived from multicellular organisms, whether vertebrate or invertebrate, may also be used as hosts. Our system involved use of baculovirus, the polyhedrin promotor system and insect cells as host cells to produce high quantities of bioactive gE. To our knowledge, we are the first to express gE in this system.

The references cited herein are all incorporated by reference.

SUMMARY OF THE INVENTION

The present invention relates to the production of HSV-1 gE, by recombinant DNA techniques, and its use as an immunogen in a vaccine to protect against HSV-1 and/or HSV-2 infections. Vaccines made from genetically engineered immunogens should be safer than conventional vaccines made from attenuated virus because there is no risk of infection to the recipient; and specifically with the herpes virus, there should be no risk of cervical cancer. Alternatively, the genetically engineered glycoprotein or protein product may be used to produce antibodies for use in passive immunotherapy. The invention also relates to the transformed cell line, which contains the subject transplacement vector, and its cultures which produce HSV-1 gE.

To this end, we constructed a recombinant baculovirus expressing high levels of HSV-1 gE in Sf9 cells. We unexpectedly discovered, however, that vaccination of mice with our expressed gE, induced high neutralizing antibody titers, a DTH response, and protection against lethal HSV-1 challenge. Methods and compositions are therefore provided for the cloning and expression of HSV gE gene in single-cell host organisms. Also described are methods for culturing these novel single-cell organisms to produce the HSV gE gene product as well as methods for the purification of the gene product.

A human host is then preferably inoculated with a vaccine comprising an immunity inducing dose of gE alone or with one or more HSV glycoproteins or proteins by the systemic route, the enteric route or by the ocular route. The vaccine may also comprise one or more adjuvants administered with, before or after the glycoprotein component of the vaccine.

The vaccine of the invention may be conveniently utilized in liquid form, freeze-dried, spray dried or lyophilized form, in combination with one or more suitable preservatives and protective agents to protect the glycoproteins or proteins during processing.

A. Antigen

The baculovirus expressed gE migrated on gels as a doublet band with apparent molecular weights of 68 and 70 kDa. The recombinant gE was glycosylated, as demonstrated by its susceptibility to tunicamycin treatment. Indirect immunofluorescence also demonstrated that it was transported to the membrane of Sf9 cells. Mice vaccinated with our expressed gE developed high serum titers of HSV-1 neutralizing antibodies, which was demonstrated by plaque reduction assays. Glycoprotein E also induced a strong delayed type hypersensitivity (DTH) response to HSV-1, and mice vaccinated with the recombinant gE were protected from both intraperitoneal and ocular lethal HSV-1 challenge.

B. Adjuvants

Vaccines are often administered in an emulsion with various adjuvants. The adjuvants aid in attaining a more durable and higher level of immunity using smaller amounts of antigen in fewer doses than if the immunogen were administered alone. The adjuvants for use in the present invention include but are not limited to alum, Freund's, MTP-PE and ISCOMs (Quil A). In addition, the vaccine may comprise a liposome or other membrane bound vesicle comprising one or more HSV-1 glycoproteins administered with or without one or more adjuvants to induce the cell mediated immune response.

C. Immunization Routes And Dosages

The vaccine can be administered by the systemic route, the ocular route either alone or in combination with systemic vaccination, or the enteric route. The systemic route includes but is not limited to subcutaneous, intramuscular or intravenous injection in one or multiple doses. The ocular route includes but is not limited to subconjunctival injection, surface drops, a slow-release device such as a collagen shield, a hydrogel contact lens or an ALZA "Ocusert" in one or multiple doses.

Doses to be administered are variable and depend on the desired effect and on the chosen administration route, with i to 3 doses generally comprising the vaccination. However, inoculation doses to humans by injection vary from about 10 µg long to 500 µg. For ocular vaccination, the human dosages vary from about 1 µg to 500 µg; whereas for enteric vaccination, the human dosages vary from about 1 µg to 800 µg.

It is therefore a general object of the present invention to express high levels of HSV-1 gE.

It is an object of the present invention to express high levels of HSV-1 gE from one virus strain in a single vector system.

It is also an object of the present invention to express high levels of bioactive HSV-1 gE from cells which have been infected or transformed with a recombinant baculovirus.

It is another object of the present invention to obtain a transformed cell line which produces HSV-1 gE.

It is a further object of the present invention to develop an effective vaccine for the treatment or prevention of HSV in a host.

These and other objects will become readily apparent to those skilled in the art from the following description and appended claims.

BRIEF DESCRIPTION OF THE DRAWINGS

The present invention will be described in connection with the accompanying drawing in which:

FIGS. 1A–1C are schematic diagrams of the construction of the pAc-gE1 recombinant baculovirus transfer vector containing the HSV-1 gE gene. FIG. 1A: Details of preparation of the recombinant vector containing the gE gene of HSV-1 strain KOS are given in the Detailed Description below. FIG. 1B: The thick solid black line indicates the extent of the 1,822 nucleotide isolated gE fragment that was inserted into the baculovirus vector. The arrow head indicates the 3' end of the gene. The dashed lines show regions removed by enzymatic digestions as indicated. The gI and US9 designations show the location of the adjacent ends of these flanking genes that have been removed. The numbers indicate the number of nucleotides in the regions indicated by brackets. The gE initiating ATG codon is 27 nucleotides from the start of the gE fragment, which in turn is 203 nucleotides from the 3' end of gI. The gE TAA termination codon is 141 nucleotides from the end of the gE fragment, which in turn is 278 nucleotides from the start of the US9 gene. Thus, the final gE construct contains no HSV-1 genes except gE and cannot produce any HSV-1 proteins other than gE. FIG. 1C: The polyhedrin gene promoter sequence near the start of the gE gene in the final vector is followed by the modified BamH I/Bcl I site (underlined), 27 noncoding nucleotides of the gE gene, and the start of the gE coding sequence (ATG).

FIGS. 2A–2B are a Western blot analysis and coomassie blue staining of baculovirus-gE. (FIG. 2A) Western blot analysis of baculovirus-gE expression and glycosylation. Insect cells were infected with the baculovirus-gE recombinant (vAc-gE1) (MOI of 10 PFU/cell for 72 hr). Vero cells were infected with HSV-1 strain KOS (MOI of 10 PFU/cell for 20 hr). Total cell lysates were analyzed by Western blots using 1BA10 monoclonal antibody (3). Lanes: M, molecular weight markers; 1, $4\times10^5$ HSV-1 infected Vero cells; 2, $4\times10^3$ vAc-gE1 infected Sf9 cells; 3, tunicamycin treated vAc-gE1 infected cells; 4, wild-type AcNPV infected insect cells; 5, mock infected Sf9 cells. All lanes shown are from the same exposure of the same gel. For the purpose of photography, lanes 4 and 5 were moved from a different location on the autoradiogram. (FIG. 2B) Detection of expressed gE by coomassie blue staining. Total cell lysates from recombinant gE or wild-type baculovirus (10 pfu/cell, 72 hr post infection) were run on 10% SDS-PAGE and stained with coomassie brilliant blue. Lanes: M, molecular weight markers; B, wild-type baculovirus infected cells; gE, vAc-gE1 infected cells 72 hr post infection. The arrows indicate the positions of expressed gE (gE) and the wild-type polyhedrin (P) protein bands.

FIG. 3 shows the neutralization of HSV-1 infectivity with anti-baculovirus-gE sera. Serial dilutions of heat-inactivated pooled sera from baculovirus-gE, mock-vaccinated (wild type baculovirus), or HSV-1 (strain KOS) inoculated mice were incubated with 100 PFU of HSV-1 strain KOS in the presence of fresh or heat-inactivated guinea pig complement as described in the text and the remaining infectious virus was titrated.

DETAILED DESCRIPTION

The present invention utilizes recombinant DNA techniques to insert a DNA sequence coding for HSV-1 gE or a portion thereof, into a DNA transplacement vector, such that the vector is capable of replicating and directing expression of the gE gene in a foreign host. The resulting recombinant DNA molecule is introduced into insect cells to enable high production of gE, or a portion or molecular variant thereof by the host cells. The gE produced is then isolated and purified for use in immunotherapy against both HSV type i and/or type 2.

The Examples set forth below describe use of baculovirus, the polyhedrin promoter system and insect cells as host cells. However, it would be well within the skill of the art to use analogous techniques to construct expression vectors for expression of desired gE and gE products In alternative host cell cultures. The following detailed description is, therefore, not to be taken in a limiting sense, and the scope of the present invention is best defined by the appended claims.

A. Viruses and Cells

The E2 strain of *Autographa californica* nuclear polyhedrosis virus (AcNPV) and *Spodoptera frugiperda* clone 9 (Sf9) cells were grown using TNM-FH containing 10% fetal bovine serum as previously described (4). Plaque purified HSV-1 (strains McKrae and KOS) and Vero cells were grown as previously described (5).

B. Construction of the AcNPV Recombinant Transfer Vector

The plasmid pSG25 is obtained by the procedure of Goldin et al. (6). Briefly, viral DNA to be used for cloning and as a hybridization probe is purified from cell-free virus. Vero cell monolayers are infected with HSV-1 (KOS). When cytopathic affect is generalized, cells are pelleted by centrifugation, resuspended in buffer, and the viral DNA is banded in CsCl. Fractions comprising the viral DNA peak (densities of 1.735 to 1.720) are then isolated by standard procedures. Resulting viral DNA is subjected to restriction enzyme digestion by EcoR1, and the restriction fragments are inserted into the single EcoR1 site of pBR325 using T4 DNA ligase. Bacteria are transformed with the resulting plasmids to obtain an HSV-1 library.

Figure 1A:
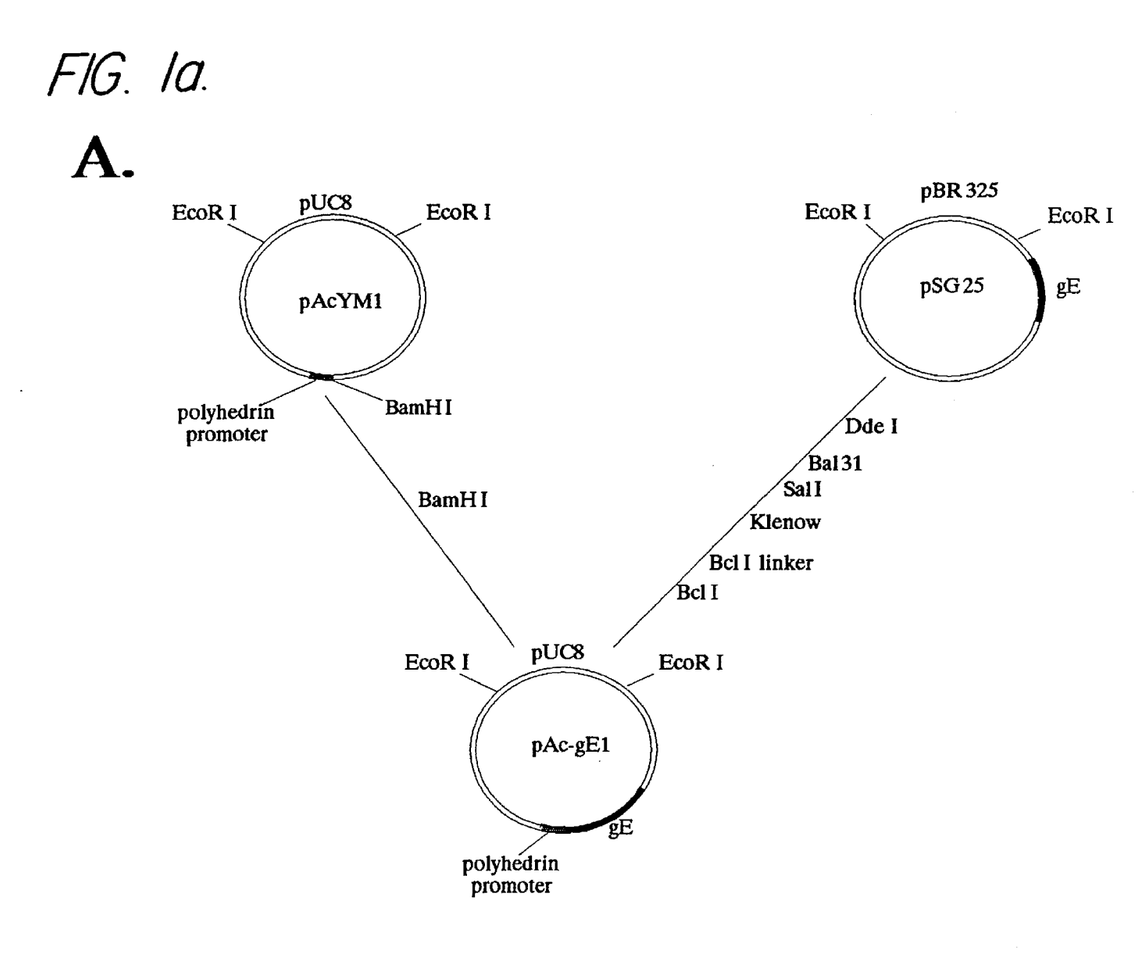
Figure 1B:
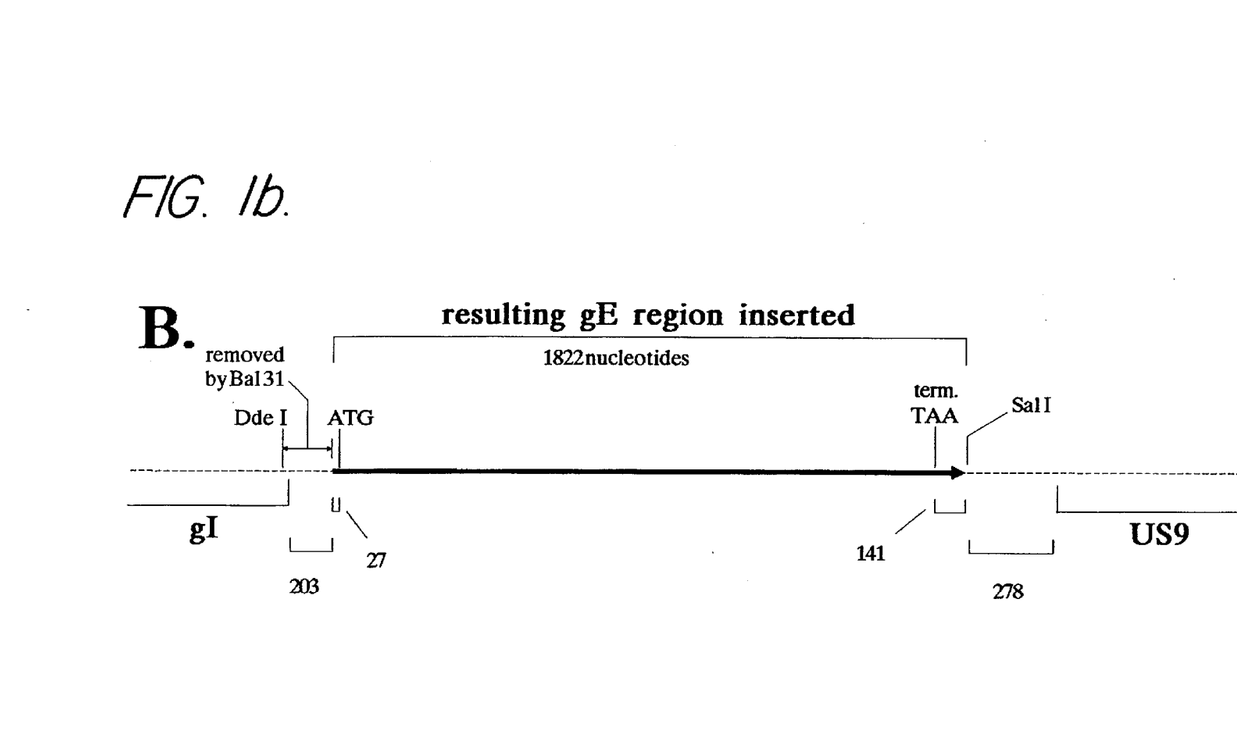
Figure 1C:
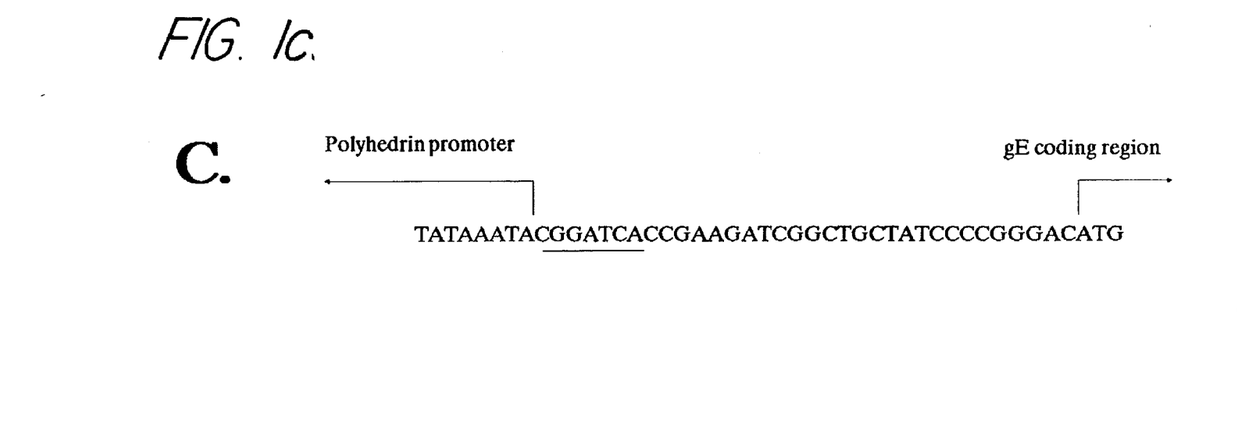

As shown in FIG. 1, plasmid pSG25 containing the EcoRI H restriction fragment from HSV-1 strain KOS (6), was digested with Dde I and a fragment containing the complete coding region of HSV-1 gE was isolated. The linearized fragment was treated with Bal 31 and then recut with Sal I. After addition of Bcl I linker the complete gE structural gene was inserted into the BamH I site of the vector pAcYM1 (4) under control of the baculovirus polyhedrin gene promoter. The bottom of the figure shows the polyhedrin gene promoter sequence of the final vector in the area of the start of the gE gene. This is followed by the modified BamH I/Bcl I site (underlined), 27 noncoding nucleotides of the gE gene, and the start of the gE coding sequence (ATG).

C. Transfection and Selection of Recombinant Viruses

Sf9 cells were cotransfected with purified infectious baculovirus (AcNPV) DNA and pAc-gE1 plasmid DNA as described (4). Following three cycles of plaque purification, three polyhedrin-negative recombinant viruses were selected. The recombinant baculoviruses all expressed gE with similar properties. One was chosen arbitrarily for further study and was designated vAc-gE1.

D. Tunicamycin Treatment

Infected cells (10 PFU/cell) were incubated in 4 ug/ml tunicamycin in TNM-FH media (J. R. H. Biosciences, Lenexa, Kans.) from 0–48 hr post infection and harvested for SDS-PAGE as described (7).

E. Western Blots

Western immunoblot analyses were carried out under denaturing conditions, as previously described (8). The nitrocellulose blots were reacted with one of the three anti-gE monoclonal antibodies Fd172 (9), 7–8 (Chatterjee et al., unpublished), 1BA10 (3) or total HSV-1 antibody (made in rabbit against purified HSV-1 virions) for 1 hour at 4° C. The blots were then incubated with $^{125}$I-protein A for 1 hour at 25° C. and autoradiographed.

F. Immunization Of Mice

Twenty Balb/c mice (6–8 weeks old) were vaccinated with freeze-thawed whole cell lysates of Sf9 cells infected with baculovirus expressing gE. Lysates from $1\times10^6$ Sf9 cells were injected subcutaneously with Freund's complete adjuvant on day 0 or with Freund's incomplete adjuvant on days 21 and 42. Intraperitoneal (i.p.) injections were given concurrently using lysates from $1\times10^6$ infected Sf9 cells in PBS. We estimate from coomassie blue staining that extract from $1\times10^6$ baculovirus-gE infected cells contains approximately 30 µg of gE. Eighteen mock vaccinated mice were inoculated with Sf9 cells infected with wild type baculovirus using the same regimen. A positive control group of eleven mice was immunized three times i.p. with $2\times10^5$ PFU of the nonvirulent HSV-1 strain KOS. Sera were collected 3 weeks after the final vaccination and pooled for each group.

For HSV-1 ocular protection studies, 5 mice/group were vaccinated twice in a similar manner using freeze-thawed whole cell lysates from $1\times10^6$ Sf9 cells infected with baculovirus expressing gE. Injections were done subcutaneously with Freund's complete adjuvant on day 0 and with Freund's incomplete adjuvant on day 21. Intraperitoneal (i.p.) injections were given concurrently using lysates from $1\times10^6$ infected Sf9 cells in PBS. Mock vaccinated mice were inoculated with Sf9 cells infected with wild type baculovirus using the same regimen. Mice in the positive control group were immunized at the same time i.p. with $2\times10^5$ PFU of the nonvirulent HSV-1 strain KOS.

G. Serum Neutralization Assay

For in vitro serum neutralization assays, heat inactivated pooled sera were diluted in MEM, mixed with 100 PFU of HSV-1 strain KOS, and incubated for 30 min at 37° C. Two and one half percent fresh or heat-inactivated guinea pig complement was added and the mixture was incubated for an additional 30 min. Duplicate samples were added to CV-1 cells in 24-well microtiter plates and residual HSV-1 infectivity was assayed. The plates were incubated at 37° C. for 72 hr, stained with 1% crystal violet, and the plaques were counted. The experiment was repeated twice and the means of the antibody titers (50% plaque reduction) were expressed as the reciprocal of the serum dilution.

H. Delayed Type Hypersensitivity (DTH)

To study the DTH response to gE, mice were vaccinated three times as described above. Twenty one days after the final vaccination, mice were injected with $2\times10^6$ PFU of uv-inactivated HSV-1 (strain McKrae) in 10 µl of MEM, in the dorsal side of the right ear. Ear thickness was measured just prior to injection and 24 h, 48 h, and 72 h after injection using a micrometer (Mitutoyo, Tokyo, Japan) and recorded as net swelling (post-challenge minus pre-challenge ear thickness) (10). Controls included HSV-1 (strain KOS) vaccinated mice (positive control) and wild type baculovirus (mock) vaccinated mice (negative control).

I. Viral Challenge

Three weeks after the final vaccination, mice were challenged i.p. with $2\times10^6$ PFU (4 LD50 by the i.p. route) or ocularly with $2 \times 10^5$ PFU/eye (10 LD50 by the ocular route) of the virulent HSV-1 strain Mckrae. Challenged mice were monitored for two weeks.

RESULTS

A. Construction of Recombinant Baculoviruses Expressing gE

The strategy for the construction of the baculovirus transfer vector (pAc-gE1) containing the complete gE open reading frame from HSV-1 strain KOS is described above and shown in FIG. 1A. FIG. 1B illustrates in more detail the extent of the gE gene present in the final baculovirus vector. The entire gE structural gene is present, with minimal additional 5' and 3' sequences. The 5' DdeI cut and subsequent Bal 31 digestion resulted in the inclusion of only 27 HSV-1 nucleotides upstream of the initial gE ATG codon. The SalI restriction cut at the 3' end resulted in the inclusion of only 141 HSV-1 nucleotides downstream of the gE TAA termination codon. The 5' end of the gE fragment begins 203 nucleotides from gI, the nearest upstream gene. The 3' end of the gE fragment ends 278 nucleotides from US9, the nearest downstream gene. Thus, the gE-baculovirus construct contains the entire structural gE gene with no additional HSV-1 genes (or portions of HSV-1 genes). No HSV-1 proteins other than gE can be expressed from this gE-baculovirus. Following cotransfection, incorporation of the vector into baculovirus, and isolation of a recombinant, the presence of HSV-1 gE DNA in the recombinant baculovirus was verified by Southern blot hybridization.

B. Identification of Expressed gE in Insect Cells

Figure 2A:
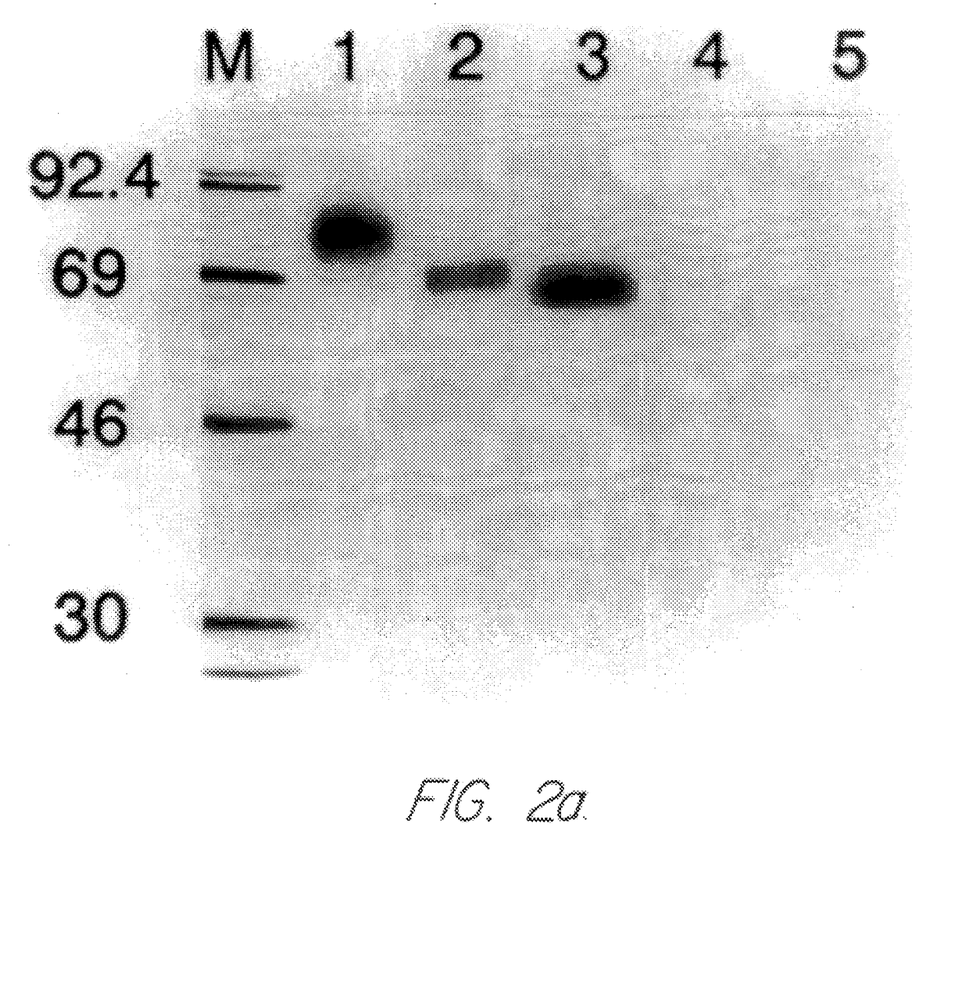
Figure 2B:
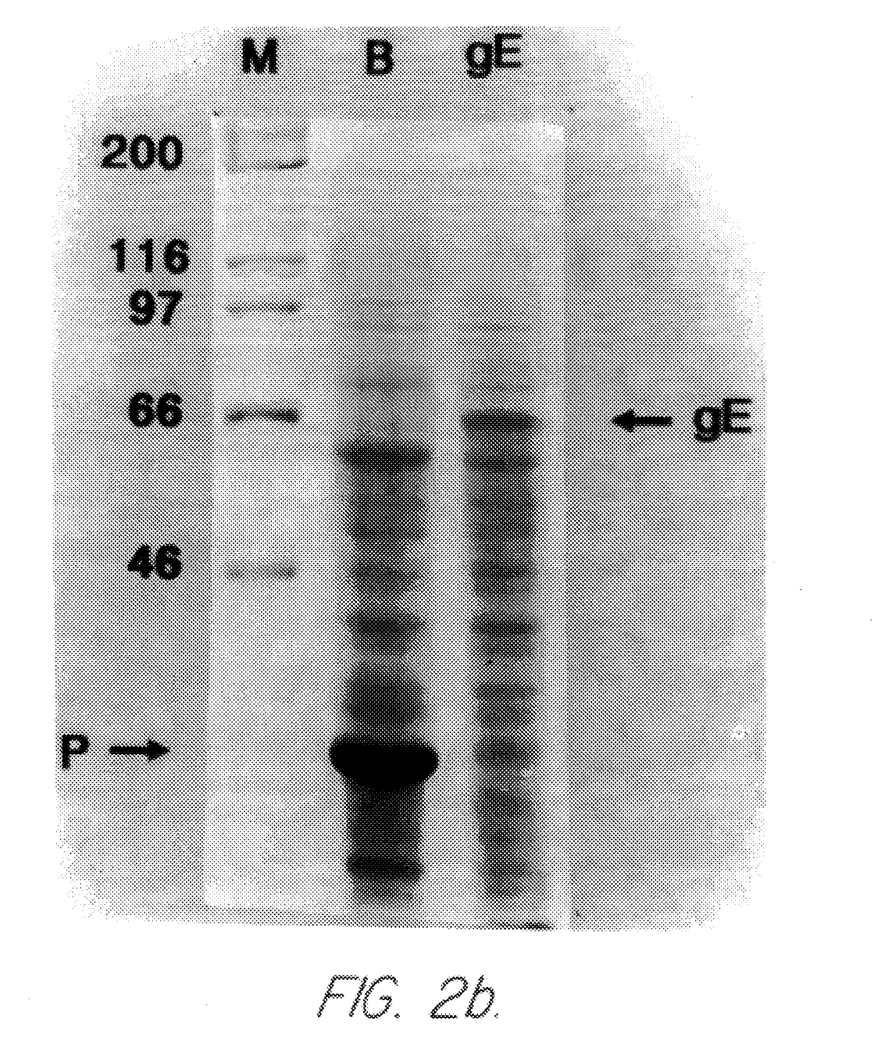

To analyze the size of baculovirus expressed gE in insect cells, total protein extracts from HSV-1 infected Veto cells or the baculovirus-gE recombinant (vAc-gE1) infected Sf9 cells were run on 10% SDS-PAGE and analyzed by Western blotting using anti-gE monoclonal antibody 1BA10 (3). This is illustrated in FIG. 2a. Glycoprotein E from HSV-1 infected Vero cells had an apparent molecular weight of 80–85 kDa (FIG. 2a, lane 1) in agreement with the previously reported apparent molecular weight of gE (2). Two bands from the baculovirus-gE extract with apparent molecular weights of 68 and 70 kDa reacted strongly with the gE specific antibody (FIG. 2a, lane 2). Similar results were seen with total HSV-1 antibody and anti-gE monoclonal antibodies Fd172 and 7–8. The level of gE expression (accumulation) seen by Western analysis was similar at 48, 72, and 96 hr post infection.

Monoclonal antibody 1BA10 (lane 2) and total HSV-1 antibody (not shown) also reacted slightly with a smaller band with an apparent molecular weight of 50 kDa (faintly seen in FIG. 2a, lane 2). Monoclonal antibodies Fd172 and 7–8 did not react with this band. The identity of this band is not clear, but it may represent agE breakdown product. Anti-gE anti serum did not react with any bands from wild type baculovirus infected cells (lane 4) or uninfected Sf9 cells (lane 5).

C. Glycosylation and Cellular Localization of Baculovirus Expressed gE

To determine if the baculovirus expressed gE underwent N-glycosylation, recombinant baculovirus infected cells were treated with tunicamycin from 0–48 hr post infection. Following tunicamycin treatment most of the 68 and 70 kDa species were replaced by two bands with apparent molecular weights of 64 and 66 kDa (FIG. 2a, lane 3). This indicates that the 68 and 70 kDa polypeptides both contained N-linked sugars. The change in gE mobility is consistent with the presence of 2 potential N-linked glycosylation sites in the gE polypeptide as determined by sequence analysis (11). The tunicamycin treated gE size is also compatible with the reported molecular weight of 66 kDa for in vitro translated gE (12).

Indirect immunofluorescence staining of gE-baculovirus infected cells was done using Fd172 anti-gE monoclonal antibody. Strong cell surface fluorescence was seen similar to authentic HSV-1 gE (13), suggesting that the expressed gE was transported to the cell surface.

D. HSV-1 Neutralization by Serum From gE Vaccinated Mice

Figure 3:
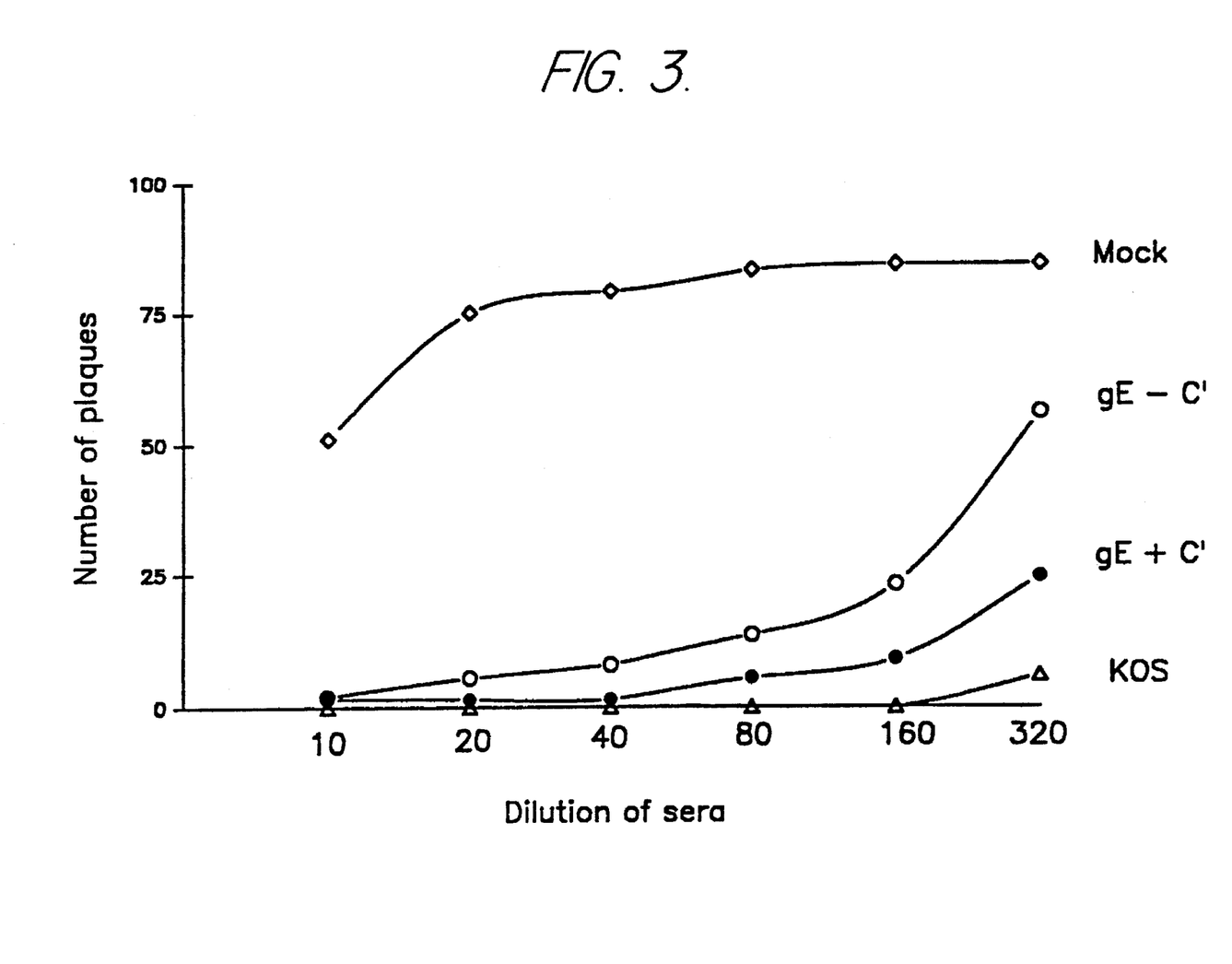

The immunogenicity of the recombinant gE was studied by immunizing mice with lysates from whole insect cells infected with baculovirus-gE as described above. These mice were also used in the i.p. challenge study below. Three weeks after the final vaccination (and prior to the i.p. HSV-1 challenge described below), mice were bled and their sera were tested for HSV-1 neutralizing activity. Pooled sera were heat-inactivated and then incubated with HSV-1 in the presence of fresh or heat-inactivated guinea pig complement. Sera from immunized mice was capable of high HSV-1 neutralizing activity in vitro (FIG. 3 and Table I). As illustrated in Table I below, neutralizing activity was higher in the presence of fresh complement (solid circles) than heat-inactivated complement (open circles). In addition, on Western blots, sera from baculovirus-gE immunized mice reacted with authentic gE from HSV-1 infected Vero cells. Thus, our baculovirus expressed gE appeared able to induce an immune response in mice that was directed against authentic gE.

TABLE I

Induction of neutralizing antibody and DTH in mice immunized with a recombinant baculovirus expressing HSV-1 gE.

| Immuniza- | Increased ear thickness[a] (mm × 10$^{-2}$) | | | Neut. Antibody[b] | |
|---|---|---|---|---|---|
| tion | 24 hr | 48 hr | 72 hr | +C' | −C' |
| vAc-gE1 | 7.0 ± 1.2 | 7.4 ± 1.5 | 14.8 ± 1.7[c] | >320 | 247 |
| KOS | 8.3 ± 1.7 | 14.7 ± 2.7 | 15.5 ± 3.2[c] | >320 | >320 |
| mock (AcNPV) | 4.8 ± 0.7 | 5.6 ± 1.2 | 8.1 ± 1.5 | <10 | <10 |

[a] Mean ± S.D. of six mice/group.
[b] Neutralization titers are expressed as the reciprocal geometric means of the dilution that produce a 50% reduction in plaque numbers.
[c] Increased ear thickness of the vAc-gE1 and KOS vaccinated mice at 72 hr. were statistically different from mock vaccinated mice by the Student t-test (p < 0.001).

E. Induction of DTH Response in gE Vaccinated Mice

To study the delayed type hypersensitivity (DTH) response to gE glycoprotein, groups of 6 mice were vaccinated three times as above and DTH responses determined as described above. Both gE and KOS vaccinated mice developed DTH responses. Ear swelling peaked at 72 hr post challenge (Table I), followed by a decline in swelling after day 3. At 72 hr the DTH response (ear swelling) in gE vaccinated mice was similar to that in HSV-1 vaccinated mice and significantly higher than the swelling in wild-type baculovirus mice (p<0.001).

F. Protection of Mice From HSV-1 Challenge By Vaccination With gE

Vaccinated mice were challenged by i.p. injection of HSV-1 strain McKrae ($2\times10^6$ PFU) three weeks after the third inoculation. As illustrated in Table II below, 95% of mice vaccinated with expressed gE (19 of 20) survived the lethal challenge, whereas only 39% of mock-vaccinated mice (7 of 18) survived. In addition, 100% of mice immunized with KOS were protected (11 of 11). Hence, the level of protection by the expressed gE was similar to that of KOS, and was significantly higher than the mock-vaccinated group (p<0.01).

TABLE II

Lethal intraperitoneal and ocular challenge of mice immunized with a recombinant baculovirus expressing HSV-1 gE.

| Immunization | i.p. challenge[a] Survival/Total | Ocular challenge[b] Survival/Total |
| --- | --- | --- |
| baculovirus-gE | 19/20[c] (95%) | 5/5[c] (100%) |
| KOS | 11/11[c] (100%) | 5/5[c] (100%) |
| mock (AcNPV) | 7/18 (39%) | 0.5 (0%) |

[a]Mice were vaccinated three times as described above and challenged i.p. with $2 \times 10^6$ PFU/mouse. Numbers in parenthesis are percent survival.
[b]Mice were vaccinated twice and challenged ocularly with $2 \times 10^5$ PFU/eye.
[c]Survival rates (protection) of the baculovirus gE and KOS vaccinated mice were significantly different from the mock vaccinated survival rate. (Fisher's Exact test, p < 0.01).

To determine whether systemic vaccination with expressed gE could also provide protection against ocular infection, mice vaccinated twice were challenged ocularly with $2\times10^5$ PFU/eye of HSV-1 strain Mckrae three weeks after the last vaccination. The mice were monitored for ten days. Five of 5 mock vaccinated mice (100%) developed significant eye disease and died following HSV-1 challenge. In contrast, all 5 of the gE and all 5 of the HSV-1 vaccinated mice survived and developed no apparent eye disease (see Table II). These results suggest that inoculation with baculovirus expressed gE can protect mice against both i.p. and ocular lethal HSV-1 challenge.

In summary, the present invention involves the high level expression of gE in a baculovirus expression system. The gE expressed in this system was glycosylated and transported to the cell surface. Antibodies raised in mice against the expressed gE neutralized the infectivity of HSV-1 in a partially complement dependent manner, and mice vaccinated with gE developed a DTH response to HSV-1. More importantly, mice systemically vaccinated with gE were protected from lethal intraperitoneal and lethal ocular HSV-1 challenge, making gE a useful and important component in any subunit vaccine against HSV-1.

G. Purification Of gE

The baculovirus expressed gE of the present invention may be purified for human use according to standard techniques (14), including but not limited to, immunoaffinity chromatography (15) and collection of secreted truncated gE from the supernatant medium of cell cultures (16).

1. Immunoaffinity chromatography

The procedures for immunoaffinity chromatography are as set forth in (15). Essentially, the gE protein was purified in roller bottles by sequential steps of lentil lectin chromatography, immunoaffinity chromatography and concentration by ultrafiltration. For the first step, 2 liters of conditioned medium was supplemented with 1 mM PMSF and 0.5% aprotinin and then loaded onto a 30-ml column of lentil lectin-Sepharose-4B (Sigma Chemical Co., St. Louis, Mo.) at a flow-rate of 50 ml/h. The column was washed sequentially with 100 ml of PBS and 100 ml of PBS containing 0.5 M NaCl. The bound fraction was eluted with PBS containing 0.5M NaCl, 0.5M α-methylmannoside, 0.1% Triton X-100, and 0.5% aprotinin, and fractions were assayed for gE by enzyme-linked immunosorbent assay (ELISA).

The peak column fractions were pooled and applied to a 10-ml immunoaffinity column prepared by linking 70 mg of a rabbit anti-gE polyclonal antibody to cyanogen bromide-activated Sepharose 4B. The gE-specific rabbit antiserum was raised against gE protein, which was purified by preparative SDS-polyacrylamide gel electrophoresis from HSV-1 infected Vero cell lysates. Prior to coupling, an IgG-enriched fraction was prepared from the gE-specific rabbit antiserum by precipitation with 33% saturated ammonium sulfate. Following application of the lectin column eluate to the immunoaffinity column, the column was washed consecutively with 20 ml of 10 mM Tris hydrochloride, pH 7.5, and 10 ml of LB without SDS and BSA and then with 30 ml of 10 mM Tris hydrochloride, pH 7.5–0.5M NaCl. The bound fraction was eluted with 3M ammonium thiocyanate, pH 7.5, and the gE protein peak was detected by ELISA and Western analysis. The peak fractions were concentrated and equilibrated in storage buffer (100 mM NaCl, 10 mM Tris hydrochloride, pH 7.5, 1 mM EDTA, 7.5% glycerol) by ultrafiltration with a PM10 membrane (Amicon Corp., Danvers, Mass.). To remove protein absorbed to the membrane surface, the membrane was washed with storage buffer plus 0.1% Triton X-100, and this wash was then combined with the initial concentrated fraction.

2. Collection of the secreted truncated gE

Procedures for the collection of the secreted trunicated gE are described in (16) and will not be repeated here. However, basically, the fragment encoding the transmembrane anchor sequence was excised from the gE gene. The deleted gE gene was then reconstructed by self-ligation to put in frame sequences coding for the extramembrane and C-terminal intracytoplasmic domains. The product was detected after transfection by immuno-precipitation of the supernatant medium of cell cultures with anti-gE monoclonal antibody.

H. Pharmaceutical Compositions

The gE of the present invention can be formulated according to known methods to prepare pharmaceutically useful compositions in admixture with a pharmaceutically acceptable carrier vehicle. Suitable vehicles and their formulation are described for example in *Remington's Pharmaceutical Sciences* by E. W. Martin. These compositions will contain an effective amount of gE together with a suitable amount of vehicle in order to prepare pharmaceutically acceptable compositions suitable for effective administration to the host.

For purely descriptive and not limiting purposes, an example of a pharmaceutical preparation of gE for parenteral administration prepared according to the present invention is described.

The vaccine may be supplied as a single dose vial of lyophilized baculovirus expressed HSV-1 gE, alone or in combination with one or more immunogenic HSV-1 glycoproteins, and a vial of diluent with alum. Alternatively, the vaccine may be supplied in a multidose vial, and a vial of diluent with alum.

The invention being described, it is clear that these methods can be modified, which modifications do not diverge from the spirit and purpose of the invention and which would be apparent to one skilled in the art. It is therefore understood that the present invention is not to be construed as limited to such, but rather to the lawful scope of the appended claims.

REFERENCES

1. BLACKLAWS, B. A., KRISHNA, S., MINSON, A. C. and NASH, A. A. Immunogenicity of Herpes simplex virus type 1 glycoproteins expressed in vaccinia virus recombinants. *Virology*, 177:727–736 (1990).

2. PARA, M. F., BAUCKE, R. B. and SPEAR, P. G. Glycoprotein gE of Herpes Simplex Virus Type 1: Effects of anti-gE on virion infectivity and on virus induced fC-binding receptors. *J.Virol.*, 41:129–136 (1982).

3. DUBIN, G., FRANK, I., and FRIEDMAN, H. M. Herpes simplex virus type 1 encodes two Fc receptors which have different binding characteristics for monomeric immunoglobulin G (IgG) and IgG complexes. *J. Virol.*, 64:2725–2731 (1990).

4. SUMMERS, M. D. and SMITH, G. E. A manual of methods for baculovirus vectors and insect cell culture procedures, Texas Agricultural Experimental Station Bulletin #1555 (1987).

5. ROCK, D. L., NESBURN, A. B., GHIASI, H., ONG, J., LEWIS, T. L., LOKENSGARD, J. R. and WECHSLER, S. L. Detection of latency related viral RNAs In trigeminal ganglia of rabbits latently Infected with herpes simplex virus type 1. *J. Virol.*, 61:3820–3826 (1987).

6. GOLDIN, A. I., SANDRI-GOLDIN, R. M., LEVINE, M. and GLORIOSO, J. C. Cloning of herpes simplex virus type I sequences representing the whole genome. *J.Virol.*, 38:50–58 (1981).

7. LASKY, L. A., DOWBENKO, D., SIMONSEN, C. C. and BERMAN, P. W. Protection of mice from lethal herpes simplex virus infection by vaccination with a secreted form of cloned glycoprotein D. *BioTech.*, 4:527–532 (1984).

8. GHIASI, H., KAIWAR, R., NESBURN, A. B. and WECHSLER, S. L. Immunoselection of recombinant baculoviruses expressing high levels of biologically active herpes simplex virus type i glycoprotein D. *Arch.Vir.*, In press (1991a).

9. CHATTERJEE, S. KOGA, J. and WHITLEY, R. J. A role for herpes simplex virus type 1 glycoprotein E in induction of cell fusion. *J.Gen.Virol.*, 70:2157–2162 (1989).

10. NASH, A. A., FIELD, H. J. and QUARTEY-PAPAFIO, R. Cell-mediated immunity in Herpes simplex virus infected mice: Induction, characterization and antiviral effects of delayed type hypersensitivity. *J.Gen.Virol.*, 48:351–357 (1980).

11. MCGEOCH, D. J., DOLAN, A., DONALD, S. and RIXON, F. J. (1985). Sequence determination and genetic content of the short unique region in the genome of Herpes Simiplex Virus Type 1. *J.Mol.Biol.*, 181:1–13 (1985).

12. LEE, G. T. Y., PARA, M. F. and SPEAR, P. G. Location of the structural genes for glycoproteins gD and gE and for other polypeptides in the S component of Herpes Simplex Virus Type 1DNA. *J.Virol.*, 43:41–49 (1982).

13. BELL, S., CRANAGE, M., BORYSIEWICZ, L. and MINSON, T. Induction of immunoglobulin G Fc receptors by recombinant vaccinia viruses expressing glycoproteins and I of herpes simplex virus type 1. *J.Virol.* 64: 2181–2186 (1990).

14. MANIATIS, T., FRITSCH, E. F. and SAMBROOK, J. Molecular Cloning: A laboratory manual. Cold Spring Harbor Laboratory, Cold Spring Harbor, N.Y.

15. PACHL, C., BURKE, R. L., STUVE, L. L., SANCHEZ-PESCADOR, L., VAN NEST, G., MASIARZ, F. and DINA, D. Expression of Cell-Associated and Secreted Forms of Herpes Simplex Virus Type 1 Glycoprotein gB in Mammalian Cells. *Jnl. Virol.*, 61(2):315–325 (1987).

16. MANSERVIGI, R., GROSSI, M. P., GUALANDRI, R., BALBONI, P. G., MARCHINI, A., ROTALA, A., RIMESSI, P., DI LUCA, D., CASSAI, E. and BARBANTI-BRODANO, G. Protection from Herpes Simplex Virus Type 1 Lethal and Latent Infections by Secreted Recombinant Glycoprotein B Constitutively Expressed in Human Cells with a BK Virus Episomal Vector. *Jnl. Virol.*, 64(1):431–436 (1990).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 1864 base pairs
      ( B ) TYPE: nucleic acid
      ( C ) STRANDEDNESS: single
      ( D ) TOPOLOGY: linear    ( i i ) MOLECULE TYPE: DNA (genomic)

( x i ) SEQUENCE DESCRIPTION: SEQ ID NO:1:

```
TATAAATACG  GATCACCGAA  GATCGGCTGC  TATCCCCGGG  ACATGGATCG  CGGGGCGGTG      60

GTGGGGTTTC  TTCTCGGTGT  TTGTGTTGTA  TCGTGCTTGG  CGGGAACGCC  CAAAACGTCC     120

TGGAGACGGG  TGAGTGTCGG  CGAGGACGTT  TCGTTGCTTC  CAGCTCCGGG  GCCTACGGGG     180

CGCGGCCCGA  CCCAGAAACT  ACTATGGGCC  GTGGAACCCC  TGGATGGGTG  CGGCCCCTTA     240
```

-continued

| | | | | | | |
|---|---|---|---|---|---|---|
| CACCCGTCGT | GGGTCTCGCT | GATGCCCCCC | AAGCAGGTGC | CCGAGACGGT | CGTGGATGCG | 300 |
| GCGTGCATGC | GCGCTCCGGT | CCCGCTGGCG | ATGGCGTACG | CCCCCCCGGC | CCCATCTGCG | 360 |
| ACCGGGGGTC | TACGAACGGA | CTTCGTGTGG | CAGGAGCGCG | CGGCCGTGGT | TAACCGGAGT | 420 |
| CTGGTTATTC | ACGGGGTCCG | AGAGACGGAC | AGCGGCCTGT | ATACCCTGTC | CGTGGGCGAC | 480 |
| ATAAAGGACC | CGGCTCGCCA | AGTGGCCTCG | GTGGTCCTGG | TGGTGCAACC | GGCCCAGTT | 540 |
| CCGACCCCAC | CCCCGACCCC | AGCCGATTAC | GACGAGGATG | ACAATGACGA | GGGCGAGGAC | 600 |
| GAAAGTCTCG | CCGGCACTCC | CGCCAGCGGG | ACCCCCGGC | TCCCGCCTCC | CCCCGCCCCC | 660 |
| CCGAGGTCTT | GGCCCAGCGC | CCCCGAAGTC | TCACATGTGC | GTGGGGTGAC | CGTGCGTATG | 720 |
| GAGACTCCGG | AAGCTATCCT | GTTTCCCCC | GGGGAGACGT | TCAGCACGAA | CGTCTCCATC | 780 |
| CATGCCATCG | CCCACGACGA | CCAGACCTAC | TCCATGGACG | TCGTCTGGTT | GAGGTTCGAC | 840 |
| GTGCCGACCT | CGTGTGCCGA | GATGCGAATA | TACGAATCGT | GTCTGTATCA | CCCGCAGCTC | 900 |
| CCAGAATGTC | TGTCCCCGGC | CGACGCGCCG | TGCGCCGCGA | GTACGTGGAC | GTCTCGCCTG | 960 |
| GCCGTCCGCA | GCTACGCGGG | GTGTTCCAGA | ACAAACCCCC | CACCGCGCTG | TTCGGCCGAG | 1020 |
| GCTCACATGG | AGCCCGTCCC | GGGGCTGGCG | TGGCAGGCGG | CCTCCGTCAA | TCTGGAGTTC | 1080 |
| CGGGACGCGT | CCCCACAACA | CTCCGGCCTG | TATCTGTGTG | TGGTGTACGT | CAACGACCAT | 1140 |
| ATTCACGCCT | GGGGCCACAT | TACCATCAGC | ACCGCGGCGC | AGTACCGGAA | CGCGGTGGTG | 1200 |
| GAACAGCCCC | TCCCACAGCG | CGGCGCGGAT | TTGGCCGAGC | CCACCCACCC | GCACGTCGGG | 1260 |
| GCCCCTCCCC | ACGCGCCCCC | AACCCACGGC | GCCCTGCGGT | TAGGGGCGGT | GATGGGGCC | 1320 |
| GCCCTGCTGC | TGTCTGCACT | GGGGTTGTCG | GTGTGGGCGT | GTATGACCTG | TTGGCGCAGG | 1380 |
| CGTGCCTGGC | GGGCGGTTAA | AAGCAGGGCC | TCGGGTAAGG | GGCCCACGTA | CATTCGCGTG | 1440 |
| GCCGACAGCG | AGCTGTACGC | GGACTGGAGC | TCGGACAGCG | AGGGAGAACG | CGACCAGGTC | 1500 |
| CCGTGGCTGG | CCCCCCCGGA | GAGACCCGAC | TCTCCCTCCA | CCAATGGATC | CGGCTTTGAG | 1560 |
| ATCTTATCAC | CAACGGCTCC | GTCTGTATAC | CCCCGTAGCG | ATGGGCATCA | ATCTCGCCGC | 1620 |
| CAGCTCACAA | CCTTTGGATC | CGGAAGGCCC | GATCGCCGTT | ACTCCAGGC | CTCCGATTCG | 1680 |
| TCCGTCTTCT | GGTAAGGCGC | CCCATCCCGA | GGCCCACGT | CGGTCGCCGA | ACTGGGCGAC | 1740 |
| CGCCGGCGAG | GTGGACGTCG | GAGACGAGCT | AATCGCGATT | TCCGACGAAC | GCGGACCCCC | 1800 |
| CCGACATGAC | CGCCCGCCCC | TCGCCACGTC | GACCGCGCCC | TCGCCACACC | CGCGACCCCC | 1860 |
| GGGC | | | | | | 1864 |

We claim:

1. A vaccine against Herpes Simplex Virus-1 infection, comprising Herpes Simplex Virus Type 1 (HSV-1) gE produced by the expression of a recombinant baculovirus having a genetic construct which comprises:
   a) a gene sequence encoding at least one of a full length HSV-1 gE (SEQ ID No. 1) and HSV-1 gE truncated by removal of a fragment encoding the transmembrane anchor sequence; and b) a promoter sequence wherein said gE gene sequence is functionally linked to the regulatory elements of said promoter, and wherein said promoter is Operative in a baculovirus expression system.

2. The vaccine of claim 1, wherein the genetic construct comprises pAc-gE.

3. The vaccine of claim 1, further comprising a pharmaceutically acceptable carrier.

4. The vaccine of claim 1, further comprising at least one adjuvant.

5. The vaccine of claim 4, wherein the adjuvant is selected from the group consisting of alum, Freund's, muramyl tripeptide phosphatidyl ethanol amine, and immunstimulating complexes.

6. The vaccine of claim 1, wherein the promoter is a polyhedron gene promoter.

7. A process for preparing a vaccine against Herpes Simplex Virus-1 infection, comprising the steps of:

preparing a recombinant baculovirus having a genetic construct which comprises a gene sequence encoding at least one of a full length Herpes Simplex Virus Type 1 (HSV-1) gE (SEQ ID No. 1) and HSV-1 gE truncated by removal of a fragment encoding the transmembrane anchor sequence and a promoter sequence wherein said gE gene sequence is functionally linked to the regulatory elements of said promoter and wherein said promoter is operative in a baculovirus expression system:

introducing the recombinant baculovirus into a first set of host cells;

culturing the host cell; and recovering said HSV-1 gE from the culture.

8. The process of claim 7 wherein said HSV-1 gE is obtained without a contamination by other products or proteins.

9. The processes of claim 7, further comprising the step of formulating an emulsion comprising HSV-1 gE and a pharmaceutically acceptable carrier.

10. The process of claim 9, wherein the emulsion includes at least one adjuvant.

11. The process of claim 10, wherein the adjuvant is selected from the group consisting of alum, Freund's, muramyl tripeptide phosphatidyl ethanolamine, and immunostimulating complexes.

12. The process of claim 7, wherein the recombinant baculovirus is prepared by integrating the genetic construct into the baculovirus genome.

13. The process of claim 12, wherein the genetic construct comprises pAc-gE.

14. The process of claim 7, wherein said first set of host cells is an insect cell which expresses said genetic construct.

15. The process of claim 14, wherein the insect cell is derived from *Spodoptera frugiperda*.

16. The process of claim 7, wherein the promoter is a polyhedron gene promoter.

17. The process of claim 7, further comprising the steps of:

cotransfecting a second set of host cells with the genetic construct and a wild type baculovirus DNA; and screening the second set of host cells to identify cells harboring recombinant baculovirus.

18. A vaccine for the treatment or prevention of Herpes Simplex Virus-1 infection comprising at least one of full length Herpes Simplex Virus Type 1 (HSV-1) gE and HSV-1 gE truncated by removal Of the transmembrane anchor sequence.

19. The vaccine of claim 18, further comprising a pharmaceutically acceptable carrier.

20. The vaccine of claim 18, further comprising at least one adjuvant.

21. The vaccine of claim 20 wherein the adjuvant is selected from the group consisting of alum, Freund's, muramyl tripeptide phosphatidyl ethanolamine, and immunostimulating complexes.

* * * * *